United States Patent
Herz et al.

(10) Patent No.: US 9,372,080 B2
(45) Date of Patent: Jun. 21, 2016

(54) ADJUSTMENT SYSTEM FOR A TRANSFER SYSTEM IN AN IN-VITRO DIAGNOSTICS SYSTEM

(71) Applicant: Siemens Healthcare Diagnostics Products GmbH, Marburg (DE)

(72) Inventors: Achim Herz, Gross-Gerau (DE); Alexander Wiedekind-Klein, Steinbach (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 78 days.

(21) Appl. No.: 13/971,280

(22) Filed: Aug. 20, 2013

(65) Prior Publication Data
US 2014/0065017 A1    Mar. 6, 2014

(30) Foreign Application Priority Data
Sep. 6, 2012 (EP) .................. 12183261

(51) Int. Cl.
| | | |
|---|---|---|
| *G01N 35/04* | (2006.01) | |
| *G01B 21/16* | (2006.01) | |
| *G01N 35/10* | (2006.01) | |

(52) U.S. Cl.
CPC ............. *G01B 21/16* (2013.01); *G01N 35/10* (2013.01); *G01N 35/109* (2013.01)

(58) Field of Classification Search
CPC ....... G01B 21/16; G01N 35/10; G01N 35/109
USPC ........ 422/50, 62–67, 500, 501; 436/174, 180, 436/808; 435/283.1, 286.1–286.7
See application file for complete search history.

(56) References Cited

U.S. PATENT DOCUMENTS

| | | |
|---|---|---|
| 3,819,888 A | 6/1974 | Duncan |
| 2003/0054543 A1 | 3/2003 | Lafferty |
| 2010/0176806 A1 | 7/2010 | O'Day |
| 2011/0086432 A1* | 4/2011 | Herz et al. ............ 436/174 |

FOREIGN PATENT DOCUMENTS

| | | |
|---|---|---|
| CH | 414798 | 6/1966 |

OTHER PUBLICATIONS

EP Search report for App. No. 12183261 dated Feb. 18, 2013.

* cited by examiner

*Primary Examiner* — Lyle Alexander
*Assistant Examiner* — Robert Eom
(74) *Attorney, Agent, or Firm* — Dugan & Dugan, PC

(57) ABSTRACT

The invention relates to an adjustment system (3) for a transfer system (1) in an in-vitro diagnostics system. The adjustment system comprises a contact element (4), which is arranged on a movable element (2) of the transfer system (1). The contact element (4) is arranged on the movable element (2) by means of a joint element (5), wherein the joint element (5) has a self-resetting design and wherein a distance measuring sensor (7, 8) is associated with a distance between the contact element (4) and the movable element (2). The adjustment system enables a quick automated adjustment.

10 Claims, 2 Drawing Sheets

ADJUSTMENT SYSTEM FOR A TRANSFER SYSTEM IN AN IN-VITRO DIAGNOSTICS SYSTEM

Figure 1:
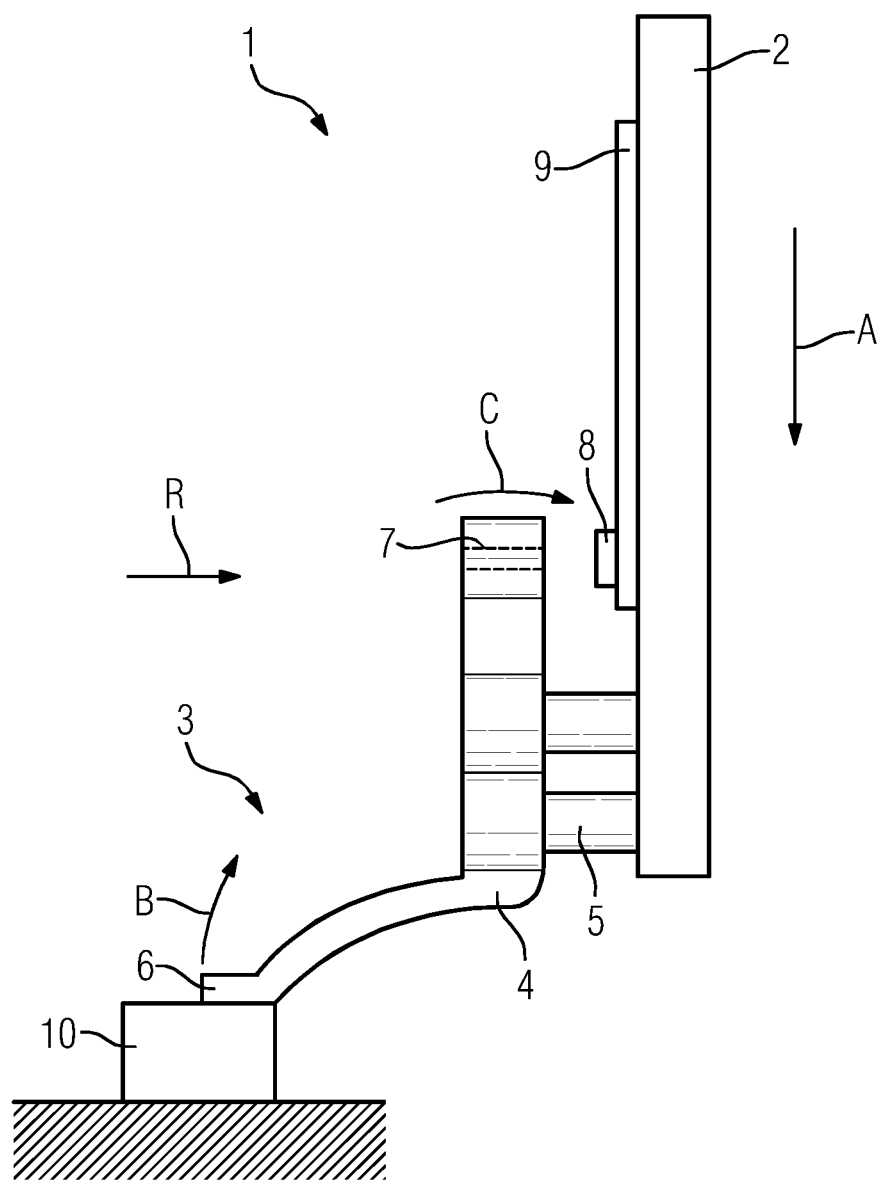

The invention relates to an adjustment system for a transfer system in an in-vitro diagnostics system, wherein the adjustment system comprises a contact element, which is arranged on a movable element of the transfer system.

These days, several detection and analysis methods for determining physiological parameters in bodily-fluid samples or in biological samples are carried out in an automated fashion in great numbers in corresponding in-vitro diagnostics systems. For this, vessels, also referred to as cuvettes, are used which are suitable for samples, reagents and also for the actual detection reaction. These usually comprise a closed wall and a possibly sealable opening for holding the respective liquid to be analyzed.

Current instruments are able to carry out a multiplicity of detection reactions and analyses with one sample. To this end, such in-vitro diagnostics systems usually comprise a holding position for a reaction vessel and an analysis system associated with the holding position. For complex test methods comprising several process steps, the sample vessel is generally transported to various addition and/or reaction stations a number of times. In order to be able to carry out a multiplicity of examinations in an automated fashion, automatic analyzers comprise transfer systems, i.e. devices for the spatial transfer of the vessels, such as e.g. transfer arms, transport belts, rotatable transport wheels or disks. Here, the instrument comprises a control unit, which, by means of appropriate software, is able largely independently to plan and work out the work steps for the desired analyses.

When assembling an in-vitro diagnostics system, there is always a certain amount of inaccuracy in respect of the positioning, particularly of the transfer systems. However, since these require exact positioning data for the automated procedure and the precise interaction, an exact adjustment is necessary. This can occur either manually with the aid of adjustment marks or else automatically.

For the purposes of the automated adjustment, there usually firstly is an appropriate sensor on the drive of the respective movable element of the transfer system to be adjusted, e.g. on a part of a transfer arm, which sensor provides information in respect of the current position of the drive to the control unit. The transfer arm is then moved in a controlled fashion toward an adjustment mark by the control unit. Previously known adjustment systems often work on a capacitive basis, with a needle on the movable element as a contact element being guided to a small metal surface on the adjustment mark. If contact is identified, the control unit stores the associated position of the drive.

An object of the present invention is to provide an adjustment system which enables a faster automated adjustment of transfer systems in an in-vitro diagnostics system.

According to the invention, this object is achieved by virtue of the contact element being arranged on the movable element by means of a joint element, wherein the joint element has a self-resetting design and wherein a distance measuring sensor is associated with a distance between the contact element and the movable element.

An advantage of the invention is that a faster automated adjustment of transfer systems in an in-vitro diagnostics system is possible if the adjustment makes do without rigid and comparatively sensitive components such as, in particular, the previously employed needles for the capacitive measurement. If the contact element is mounted on a movable element of the transfer system and has a self-resetting design, i.e. the joint develops resetting forces in the case of a deflection from a defined rest position, e.g. by virtue of springs or other elastic components, contact can be established by the deflection of the contact element and the joint. To this end, a distance measuring sensor is associated with a distance between the contact element and the movable element. In so doing, the distance measuring sensor by no means needs to be able to establish a continuously correct absolute value for the distance, but rather a simple determination of a relative change in the distance is sufficient. This is because contact with a defined adjustment mark in the in-vitro diagnostics system can already be identified by a deflection from the rest position and positional adjustment can thus be carried out.

The distance measuring sensor advantageously comprises a Hall sensor and a magnet. Here, the magnet is respectively attached to one of the components and the Hall sensor is attached to the other component. A change in the relative position between the magnet and the Hall sensor brings about a change in the generated magnetic field in the Hall sensor and thus allows identification of the contact element contacting an adjustment mark. Here, the change in the relative position of the magnet with respect to the Hall sensor can be captured quantitatively since the magnet and the Hall sensor are each attached to one of the components. As a result of the self-resetting properties of the joint element, the magnet is always at the same distance from the Hall sensor without contacting the contact element, and so the same magnetic field is applied at all times here. A magnetic distance sensor system is advantageous, in particular over a capacitive one, in that it is particularly resistant to external influences by electromagnetic fields, e.g. from cell phones.

Here, the Hall sensor is advantageously arranged on the movable element and the magnet is arranged on the contact element. In principle, the design for measuring the distance is symmetrically interchangeable. However, the magnet is merely a passive element while the Hall sensor constitutes the active, signal-producing element. Since the signals are in any case routed over the movable element and the drive thereof into the control unit, such an attachment reduces the signal paths and simplifies the construction.

In an advantageous embodiment, the joint element is designed for a multi-dimensional movement. This results in a significant simplification of the adjustment since the adjustment can be carried out in each spatial direction with the same contact element. Although the movement direction of the joint changes when the contact element contacts an adjustment mark, depending on the direction of the approach, the contact is in any case connected with a change in distance, to which the distance measuring sensor reacts.

In a particularly advantageous embodiment, the joint element comprises a rubber body, which connects the contact element and the movable element. The result of this is a particularly simple embodiment of the joint element since rubber is connected with advantageous properties: the joint lasts a long time and requires little servicing, the rubber enables movement in each dimension and returns independently to the rest position due to the elasticity thereof.

A transfer system, more particularly a transfer arm, typically has a functional apparatus, which is typically arranged at the end of the transfer arm and has a different design, depending on the specific use of the transfer arm. This functional apparatus is advantageously arranged on the contact element. On the one hand, this increases the accuracy of the adjustment since the functional apparatus is precisely the component of the transfer system which interacts with other components of the in-vitro diagnostics system and must therefore be adjusted precisely. On the other hand, the self-resetting joint element acts as a suspension for the functional apparatus, which can be desired when interacting with other components of the in-vitro diagnostics system.

The functional apparatus advantageously comprises a gripper apparatus for gripping sample or reagent vessels and/or a pipetting apparatus for transporting liquids.

In a further advantageous embodiment, in respect of the joint element, the functional apparatus is arranged on a side facing away from the distance measuring sensor. As a result, the contact element practically acts as a lever over the joint element. As a result, the distance of the distance measuring sensor from the joint element can be increased, as a result of which the deflection of the distance measuring sensor also increases. This improves the accuracy of the measurement.

A transfer system for an in-vitro diagnostics system advantageously comprises an adjustment system as described above. An automated in-vitro diagnostics system advantageously likewise comprises such a transfer system and/or an adjustment system as described above.

In particular, the advantages achieved by the invention consist of small mechanical movements in all three dimensions being able to be captured as a result of using a contact element with a distance measuring sensor, attached via a joint, leading to a faster and more exact adjustment being possible. In particular, a manual adjustment is no longer necessary. The instrument can automatically capture the current state and utilize the factors established thereby immediately and without assistance by a user being required. Here, there are no restrictions on the movement direction since an adjustment is possible in all three spatial directions.

Figure 2:
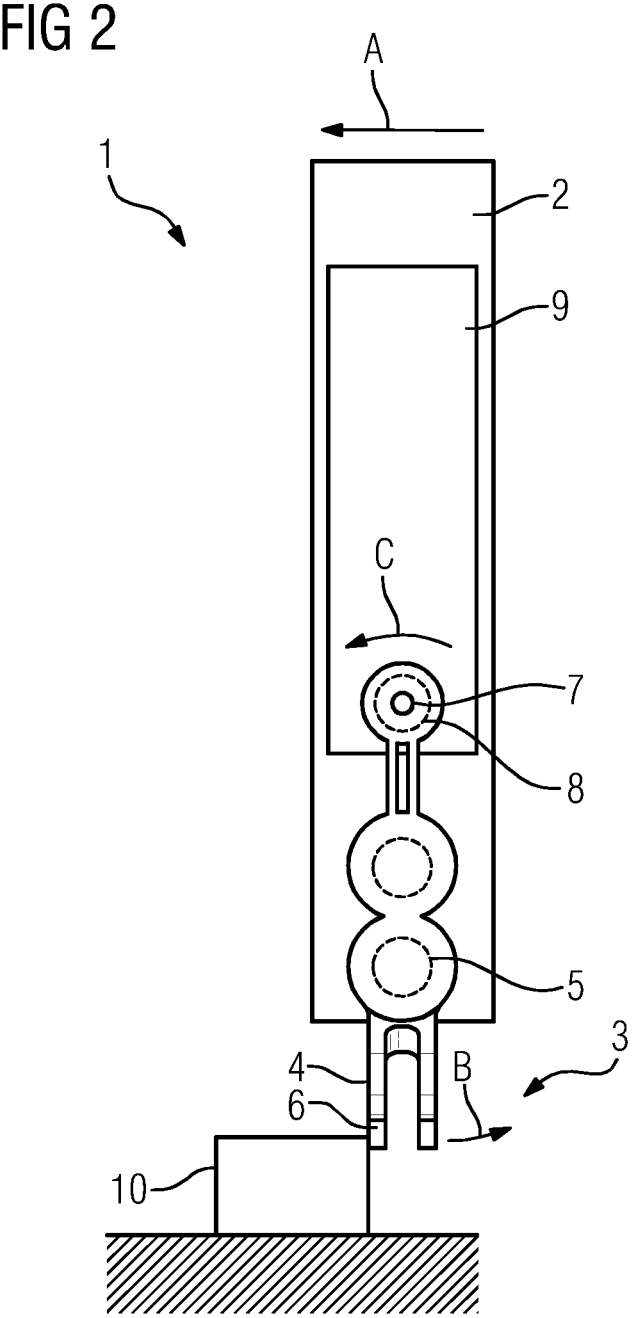

The invention will be explained in more detail on the basis of a drawing, in which:

FIG. 1 shows a schematic illustration of a transfer system in the form of a transfer arm during the automatic adjustment in a first spatial direction and FIG. 2 shows a schematic illustration of the transfer system during the automatic adjustment in a second spatial direction.

The same parts are provided with the same reference signs in all figures.

FIG. 1 shows a schematic illustration of a transfer system 1 in the form of a transfer arm in an in-vitro diagnostics system (not illustrated). The transfer system 1 comprises a movable element 2, which can be moved freely by a drive (not illustrated in any more detail). The control of the movable element is controlled by a control unit (likewise not illustrated in any more detail). There are appropriate sensors on the drive, which supply the control unit with information in respect of the current position of the drive.

For the exact adjustment of the transfer system 1, provision is made for an adjustment system 3, which comprises a contact element 4 which is attached to the movable element 2 of the transfer system 1 by means of a joint element 5. The joint element 5 consists of two rubber blocks, which at a distance respectively connect the contact element 4 and the movable element 2. The joint element 5 thus enables a multi-dimensional movement of contact element 4 and movable element 2 in relation to one another, but independently returns to the rest position.

Arranged on the contact element 4 is a functional apparatus 6 designed as a cuvette gripper. It serves to grip sample or reagent vessels. These are then transported within the in-vitro diagnostics system by means of the transfer system 1. A magnet 7 is arranged at the end of the contact element 4 distant from the functional apparatus 6. In the opposing region on the movable element 2, a Hall sensor 8 on a printed circuit board 9 is associated with the magnet 7. The Hall sensor 8 detects changes in the relative position of the magnet 7 in each direction by the change in the magnetic field and feeds this information to the control unit via the printed circuit board 9. Magnet 7 and Hall sensor 8 therefore form a distance measuring sensor.

The adjustment is carried out by virtue of the contact element 4 being led to an adjustment mark 10. In FIG. 1, the transfer system is moved in the direction A. At the position to be determined, the contact element 4 with the functional apparatus 6 butts against the adjustment mark 10. At this moment, the contact element 4 carries out an evasion movement B. This is possible as a result of the elasticity of the joint element 5. In the rest position, the magnet 7 in the contact element 4 and the Hall sensor 8 are at a specific distance from one another. The evasion movement of the contact element 4 results in a change in this distance, illustrated by the movement C. This changes the magnetic field strength measured by the Hall sensor 8. The position of the adjustment mark 10 has therefore been identified and is evaluated by the control unit for adjustment purposes.

FIG. 2 shows the transfer system 1 from FIG. 1 from the direction R, illustrated in FIG. 1 in a semitransparent illustration. All components from FIG. 1 are also illustrated here; however, FIG. 2 shows that an adjustment in other spatial directions is also possible. The direction of the movement to the adjustment mark 10 is once again illustrated as movement A, wherein the movement A is now perpendicular to the movement A in FIG. 1. An adjustment in this direction is also possible without changing the adjustment system 3, as illustrated by the movements B and C.

LIST OF REFERENCE SIGNS

1 Transfer system
2 Movable element
3 Adjustment system
4 Contact element
5 Joint element
6 Functional apparatus
7 Magnet
8 Hall sensor
9 Printed circuit board
10 Adjustment mark

The invention claimed is:

1. An adjustment system for use in a transfer system of an in-vitro diagnostics system, the adjustment system comprising:
   a contact element having a first end and an opposite second end;
   a joint element attached to the contact element at the second end; and
   a distance measuring sensor; wherein:
   the joint element is configured to be connected to a movable element and has a self-resetting design, and
   the distance measuring sensor is associated with a distance between the contact element and the movable element, and is located at the first end of the contact element away from the joint element.

2. The adjustment system as claimed in claim 1, wherein the distance measuring sensor comprises a Hall sensor and a magnet.

3. The adjustment system as claimed in claim 2, wherein the Hall sensor is configured to be arranged on the movable element and the magnet is arranged on the contact element.

4. The adjustment system as claimed in claim 1, wherein the joint element is designed for a multi-dimensional movement.

5. The adjustment system as claimed in claim 1, wherein the joint element comprises a rubber body, which is configured to connect the contact element to the movable element.

6. The adjustment system as claimed in claim 1, wherein a functional apparatus is arranged on the contact element.

7. The adjustment system as claimed in claim 6, wherein the functional apparatus comprises a gripper apparatus and/or a pipetting apparatus.

8. The adjustment system as claimed in claim 6, wherein, in respect of the joint element, the functional apparatus is arranged on a side facing away from the distance measuring sensor.

9. A transfer system for an in-vitro diagnostics system comprising one or more of transfer arms, transport belts, and rotatable transport wheels or disks; and the adjustment system of claim 1 wherein the contact element is connected to the movable element via the joint element.

10. An automated in-vitro diagnostics system comprising at least one reaction station, a control unit, a transfer system, and the adjustment system of claim 1, wherein the movable element is connected to the contact element of the adjustment system via the joint element.

\* \* \* \* \*